(12) United States Patent
McKay

(10) Patent No.: US 9,022,957 B2
(45) Date of Patent: May 5, 2015

(54) FOOT REST, METHOD FOR THE MANUFACTURE THEREOF, DEVICE INCLUDING THE FOOT REST, AND THERAPEUTIC METHOD USING THE SAME

(75) Inventor: Scott McKay, Ellington, CT (US)

(73) Assignee: Ankleaid, LLC, Ellington, CT (US)

( * ) Notice: Subject to any disclaimer, the term of this patent is extended or adjusted under 35 U.S.C. 154(b) by 512 days.

(21) Appl. No.: 13/480,706

(22) Filed: May 25, 2012

(65) Prior Publication Data

US 2013/0317396 A1 Nov. 28, 2013

(51) Int. Cl.
*A61H 1/00* (2006.01)
*A61F 7/00* (2006.01)

(52) U.S. Cl.
CPC ............. *A61F 7/0053* (2013.01); *Y10T 29/53* (2015.01); *A61F 2007/0044* (2013.01); *A61F 2007/0045* (2013.01)

(58) Field of Classification Search
CPC . A61H 1/00; A61F 7/0053; A61F 2007/0044; A61F 2007/0045; Y10T 29/53
USPC ............. 601/5, 15, 22, 23, 27, 28, 29, 30, 31, 601/32, 33, 34, 45, 55, 104, 154, 158, 160, 601/166; 297/423.1, 423.25, 423.34, 297/423.35, 423.36, 423.17; 4/538, 619, 4/622; 29/700
See application file for complete search history.

(56) References Cited

U.S. PATENT DOCUMENTS

| | | |
|---|---|---|
| 5,010,878 A | 4/1991 | Kline et al. |
| 6,315,696 B1 | 11/2001 | Garrioch |
| 6,790,188 B2 | 9/2004 | Chen |
| 6,805,678 B2 | 10/2004 | Cafaro |
| 2009/0030355 A1 | 1/2009 | Gay |
| 2010/0324611 A1 | 12/2010 | Deming et al. |
| 2011/0240797 A1* | 10/2011 | Behe ........................ 297/423.35 |

FOREIGN PATENT DOCUMENTS

WO 2004071373 A1 8/2004

* cited by examiner

*Primary Examiner* — Quang D Thanh
(74) *Attorney, Agent, or Firm* — Cantor Colburn LLP

(57) ABSTRACT

A foot rest including: a foot receptacle, the foot receptacle including a first portion and a second portion, and wherein the first portion intersects the second portion; a cross-member disposed on a first side of the first portion; and a bucket connector disposed on the first side of the first portion of the foot receptacle, wherein the cross-member is proximate an end of the first portion and the bucket connector is distal to the end of the first portion.

18 Claims, 15 Drawing Sheets

FOOT REST, METHOD FOR THE MANUFACTURE THEREOF, DEVICE INCLUDING THE FOOT REST, AND THERAPEUTIC METHOD USING THE SAME

BACKGROUND (1) Field

This disclosure relates to a foot rest, methods of manufacture of the foot rest, and therapeutic methods using the foot rest.

(2) Description of the Related Art

Cryotherapy and thermotherapy are methods of treating injuries. Application of cold tends to reduce swelling, reduce pain, and reduce tissue damage. Application of heat can provide desirable effects including pain relief, increased flexibility, reduced joint stiffness, relief of muscle spasms, and reduced inflammation.

Various ice packs, bandages, and hot and cold compresses have been developed for administering cryotherapy and thermotherapy to ankles. Nonetheless such devices can be inconvenient and uncomfortable to use. Thus there remains a need for a device for administering cryotherapy or thermotherapy to ankles that provides improved comfort and convenience.

SUMMARY

Disclosed is a foot rest including: a foot receptacle, the foot receptacle including a first portion and a second portion, wherein the first portion intersects the second portion; a cross-member disposed on a first side of the first portion; and a bucket connector disposed on the first side of the first portion of the foot receptacle, wherein the cross-member is proximate an end of the first portion and the bucket connector is distal to the end of the first portion.

Disclosed is a therapy device including, a bucket; and the foot rest disposed on the bucket, wherein the bucket connector engages a rim of the bucket and the cross-member engages an inner surface of the bucket.

Disclosed is method of manufacturing a foot rest for therapy, the method including: providing a foot receptacle, the foot receptacle including a first portion and a second portion, wherein the first portion intersects the second portion; disposing a cross-member on a first side of the first portion, wherein the cross-member is proximate an end of the first portion; and disposing a bucket connector on the first side of the first portion of the foot support, wherein the bucket connector is distal to the end of the first portion to manufacture the foot rest for therapy.

Also disclosed is a method of therapy, the method including: providing the therapy device; disposing a composition having a temperature of about −20° C. to about 50° C. in the bucket; and immersing an ankle in the composition to administer therapy to the ankle.

Also disclosed is a method of manufacturing a foot rest for therapy, the method comprising molding the therapy device disclosed above.

BRIEF DESCRIPTION OF THE DRAWINGS

The disclosed subject matter is particularly pointed out and distinctly claimed in the claims at the conclusion of the specification. The foregoing and other aspects, features, and advantages of the disclosed embodiments will become more apparent from the following detailed description taken in conjunction with the accompanying drawings in which:

Figure 1:
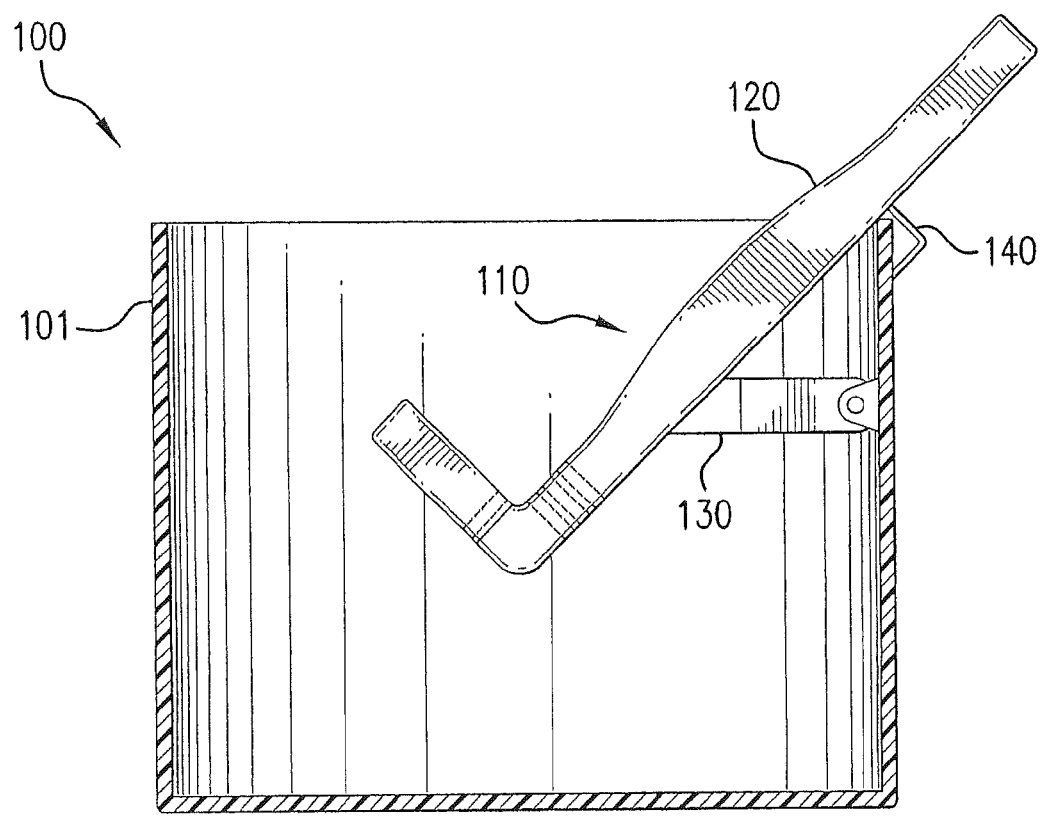
FIG. 1 is a schematic diagram of an embodiment of a therapy device.

The detailed description explains the preferred embodiments, together with advantages and features, by way of example with reference to the drawings.

DETAILED DESCRIPTION

The invention now will be described more fully hereinafter with reference to the accompanying drawings, in which various embodiments are shown. This invention may, however, be embodied in many different forms, and should not be construed as limited to the embodiments set forth herein. Rather, these embodiments are provided so that this disclosure will be thorough and complete, and will fully convey the scope of the invention to those skilled in the art Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms "first," "second," "third" etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

Disclosed herein is a foot rest comprising: a foot receptacle, the foot receptacle comprising a first portion and a second portion, wherein the first portion intersects the second portion; a cross-member disposed on a first side of the first portion; and a bucket connector disposed on the first side of the first portion of the foot receptacle, wherein the cross-member is proximate (i.e., adjacent or nearer to) an end of the first portion and the bucket connector is distal to (i.e., farther from) the end of the first portion. Also disclosed is a therapy device comprising a bucket; and the foot rest disposed on the bucket, wherein the bucket connector engages a rim of the bucket and the cross-member engages an inner surface of the bucket.

An embodiment of the therapy device 100 is shown schematically in FIG. 1. The therapy device 100 comprises a bucket 101 and a foot rest 110 disposed on the bucket.

Figure 2:
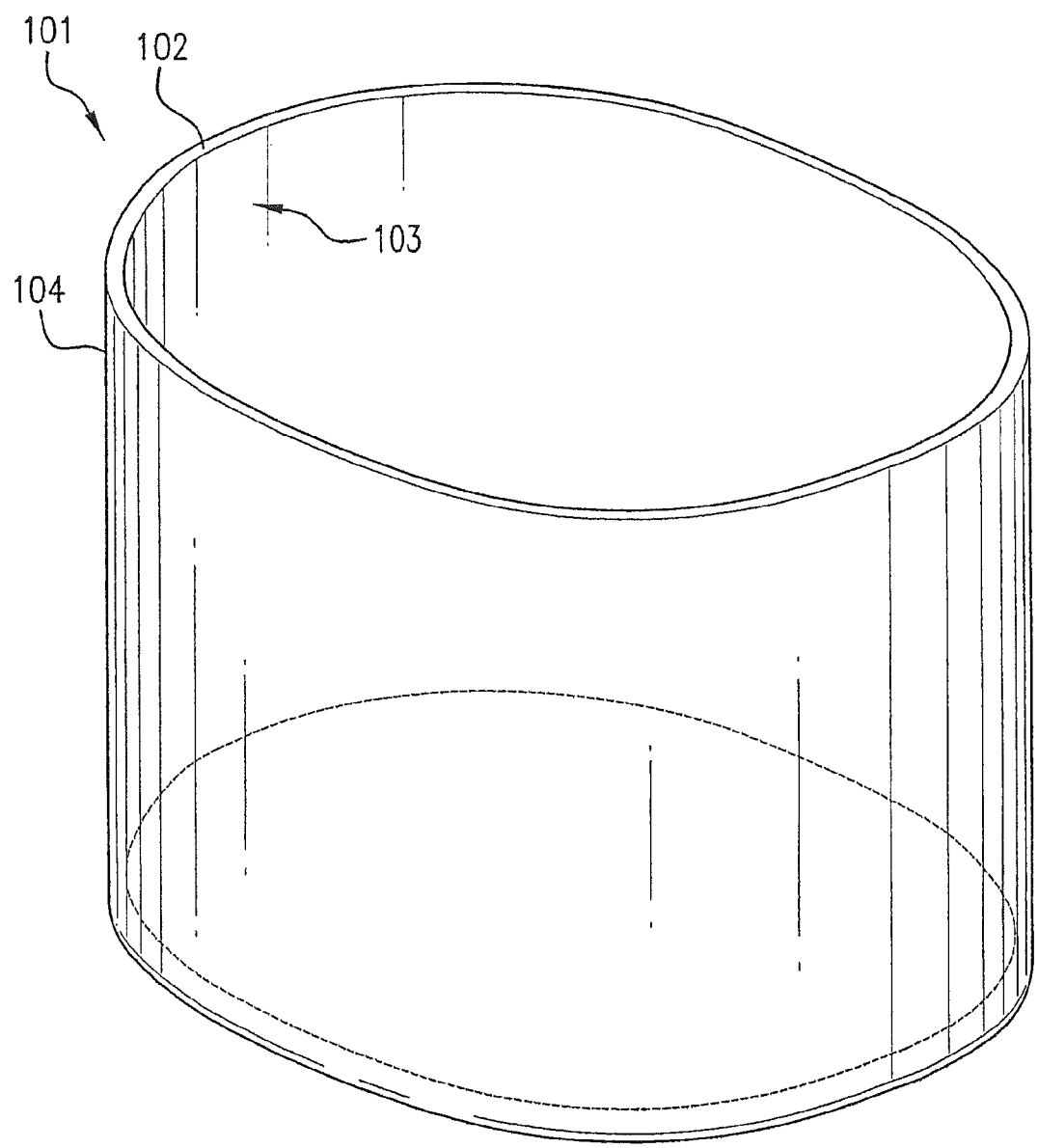
FIG. 2 is a perspective view of an embodiment of a bucket.

An embodiment of the bucket 101 is further illustrated in FIG. 2. The bucket has a rim 102, an inner surface 103, and an outer surface 104. The bucket may have any suitable shape, and may be cylindrical, square, rectangular, or oblong. An oblong bucket, i.e., a bucket in which a length and a width which are unequal, is specifically mentioned. Also, the bucket may be constructed of any suitable material, and may comprise a plastic, rubber, metal, ceramic, or wood. A plastic bucket is specifically mentioned. The bucket may have any suitable size, e.g., a length of about 30 centimeters (cm) to about 60 cm, a width of about 20 cm to about 60 cm, and a height of about 20 cm to about 80 cm. A bucket having a length of about 40 cm, a width of about 30 cm, and a height of about 30 cm is specifically mentioned. Also, a side of the bucket may have any suitable angle with respect to a bottom of the bucket. The side may form an angle about 90° to about 120° with respect to the bottom of the bucket. An embodiment in which the side forms an angle of 100° with the bottom of the bucket is specifically mentioned. In addition, the bucket may further comprise a line, i.e., a fill line that indicates a preferred level of a composition to be disposed in the bucket.

Any suitable plastic may be used. The plastic may comprise a polyacetal, polyolefin, polyacrylic, polycarbonate, polystyrene, polyester, polyamide, polyamideimide, polyarylate, polyarylsulfone, polyethersulfone, polyphenylene sulfide, polyvinyl chloride, polysulfone, polyimide, polyetherimide, polytetrafluoroethylene, polyetherketone, polyether etherketone, polyether ketone ketone, polybenzoxazole, polyphthalide, polyacetal, polyanhydride, polyvinyl ether, polyvinyl thioether, polyvinyl alcohol, polyvinyl ketone, polyvinyl halide, polyvinyl nitrile, polyvinyl esters polysulfonate, polysulfide, polythioester, polysulfone, polysulfonamide, polyurea, polyethylene terephthalate, a fluorinated polymer, or a combination thereof.

Representative rubbers include an acrylonitrile, styrene, diene, styrene-butadiene, polybutadiene, natural rubber, neoprene, and isoprene.

The plastic or rubber may further comprise an additive, such as antioxidants, such as, for example, organophosphites, for example, tris(nonyl-phenyl)phosphite, tris(2,4-di-t-butylphenyl)phosphite, bis(2,4-di-t-butylphenyl)pentaerythritol diphosphite or distearyl pentaerythritol diphosphite, alkylated monophenols, polyphenols and alkylated reaction products of polyphenols with dienes, such as, for example, tetrakis[methylene(3,5-di-tert-butyl-4-hydroxyhydrocinnamate)] methane, 3,5-di-tert-butyl-4-hydroxyhydrocinnamate octadecyl, 2,4-di-tert-butylphenyl phosphite, butylated reaction products of para-cresol and dicyclopentadiene, alkylated hydroquinones, hydroxylated thiodiphenyl ethers, alkylidene-bisphenols, benzyl compounds, esters of beta-(3,5-di-tert-butyl-4-hydroxyphenyl)-propionic acid with monohydric or polyhydric alcohols, esters of beta-(5-tert-butyl-4-hydroxy-3-methylphenyl)-propionic acid with monohydric or polyhydric alcohols; esters of thioalkyl or thioaryl compounds, such as, for example, distearylthiopropionate, dilaurylthiopropionate, ditridecylthiodipropionate, amides of beta-(3,5-di-tert-butyl-4-hydroxyphenyl)-propionic acid; fillers and reinforcing agents, such as, for example, silicates, $TiO_2$, fibers, glass fibers (including continuous and chopped fibers), carbon black, graphite, calcium carbonate, talc, mica and other additives such as, for example, mold release agents, UV absorbers, stabilizers such as light stabilizers and others, lubricants, plasticizers, pigments, dyes, colorants, anti-static agents, blowing agents, flame retardants, impact modifiers, among others. A combination thereof may be used.

Other fillers used in the conventional compounding of polymers and plastics may also be included. Examples of such fillers well known in the art include those described in "Plastic Additives Handbook, 5$^{th}$ Edition" Hans Zweifel, Ed, Carl Hanser Verlag Publishers, Munich, 2001, the contents of which are herein incorporated by reference in its entirety. Non-limiting examples of fillers include silica powder, such as fused silica and crystalline silica; boron-nitride powder and boron-silicate powders; alumina, and magnesium oxide (or magnesia); and fillers such as wollastonite including surface-treated wollastonite, calcium sulfate (as its anhydride, dihydrate or trihydrate), calcium carbonate including chalk, limestone, marble and synthetic, precipitated calcium carbonates, generally in the form of a ground particulates; talc, including fibrous, modular, needle shaped, and lamellar talc; glass spheres, both hollow and solid; kaolin, including hard, soft, calcined kaolin, and kaolin comprising various coatings known in the art; as well as mica, feldspar, silicate spheres, flue dust, cenospheres, fillite, aluminosilicate (armospheres), natural silica sand, quartz, quartzite, perlite, tripoli, diatomaceous earth, synthetic silica, and the like. All of the above fillers may be coated with a layer of metallic material or surface treated with a silane to improve adhesion and dispersion.

An embodiment in which the plastic is a glass filled polypropylene is specifically mentioned.

The metal may comprise aluminum, iron, copper, zinc, magnesium, nickel, brass, bronze, tin, or an alloy thereof. Representative alloys include steel and stainless steel.

Figure 3:
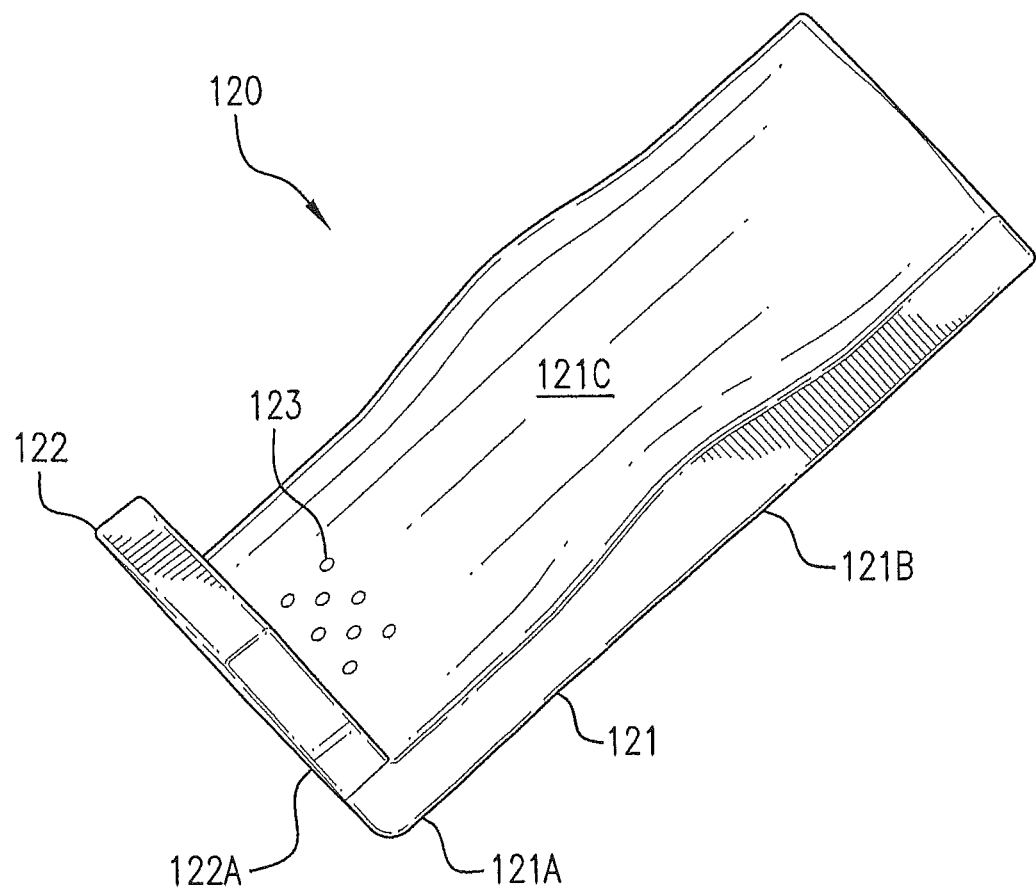
FIG. 3 is a perspective view of an embodiment of the foot receptacle.

In an embodiment, the foot rest 110 comprises a foot receptacle 120, an embodiment of which is further illustrated in FIG. 3. The foot receptacle 120 comprises a first portion 121 and a second portion 122, which intersects the first portion 121. In an embodiment, an end 121A of the first portion 121 intersects an end 122A of the second portion 122 to form a cradle or vee shape. The first portion 121 and the second portion 122 may form an angle of about 120° to about 60°, specifically about 110° to about 70°, more specifically about 100° to about 80°. An embodiment in which the first portion 121 and the second portion 122 of the foot support are perpendicular is specifically mentioned. The foot receptacle may have dimensions suitable to accommodate feet of various sizes, e.g., feet having a European size of 20 to 60, specifically 33 to 50, e.g., U.S. children's' size 0 to 13, U.S. Women's' size 3 to 20, or U.S. Men's' size 5 to 22. The first portion and the second portion may have any suitable dimension, so long as the advantageous features of the foot rest are not substantially degraded. In an embodiment, the first portion 121 may have a length of about 10 cm to about 75 cm, specifically about 30 cm to about 60 cm; a width of about 5 cm to about 30 cm, specifically about 8 cm to about 15 cm; and a thickness of about 0.5 cm to about 10 cm, specifically about 1 cm to about 5 cm.

The first portion 121 and the second portion 122 may be distinct members which are connected by a fastener. Representative fasteners include a screw, rivet, nail, pin, weld, adhesive, or a combination thereof. In another embodiment the foot receptacle 120 may be a single unitary indivisible part, i.e., a same member, as may be produced by molding, for example.

The first portion and/or the second portion may each independently be contoured to accommodate a calf, a foot, or a combination thereof. In an embodiment, the first portion 121 is contoured such that a middle portion 121B of an edge of the first portion is thicker than the end portion 121A of the first portion 121, and the middle portion 121B of the edge of the first portion is thicker than a middle portion 121C of the first portion 121. In an embodiment, the contour may be asymmetrical, and the contour may be shaped to correspond to a right foot or a left foot, for example. An embodiment in which the first portion is flat, e.g., planar and does not have a contour, is specifically mentioned.

The first portion may further comprise a vent 123 if desired. The first portion may include a plurality of vents or a single vent. Also, the size of the vent is not limited so long as it does not detract from the desirable properties of the first portion. The vent may have a cross-sectional area of about 0.1 cm to 10 cm$^2$, specifically 1 cm$^2$ to 3 cm$^2$.

Figure 4:
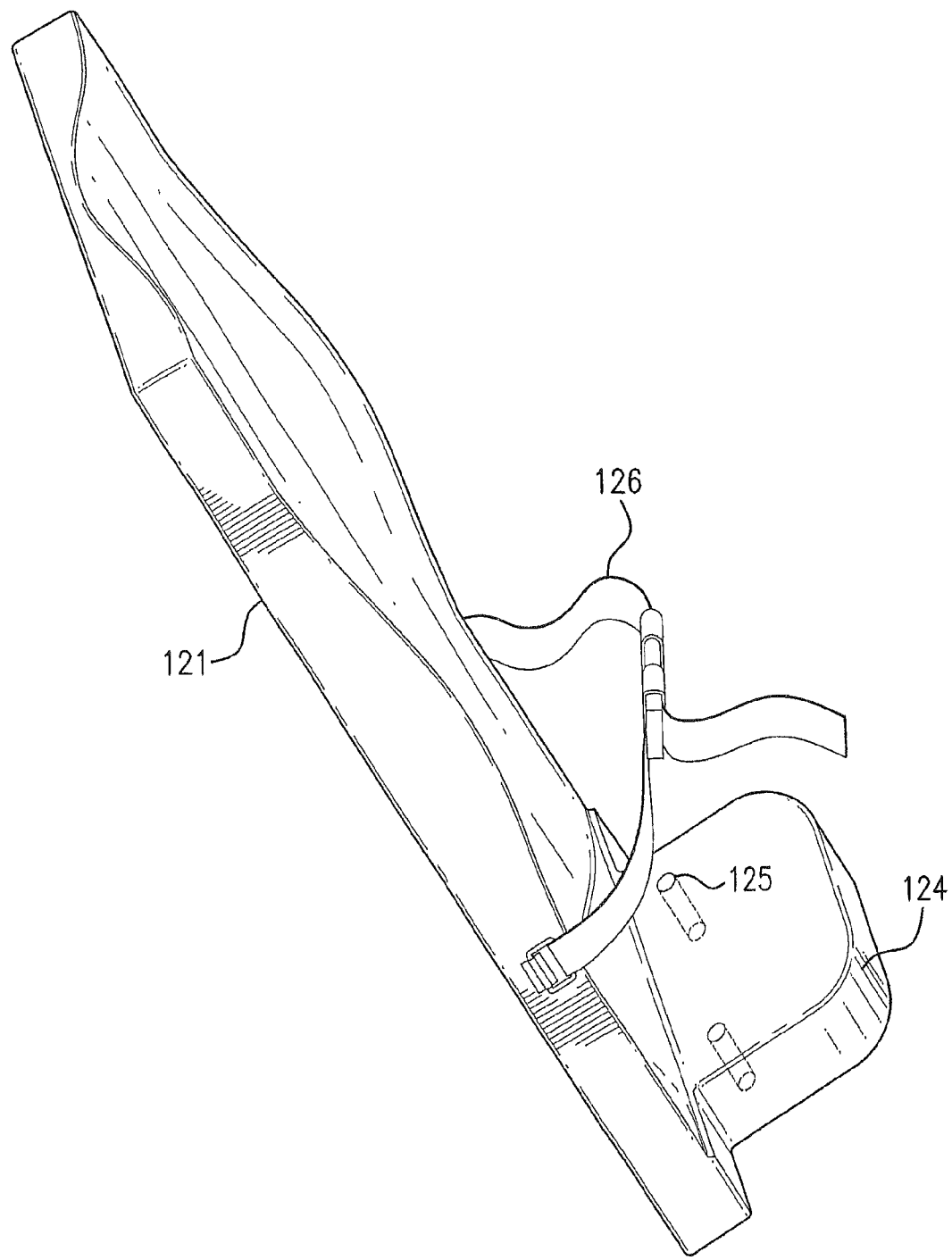
FIG. 4 is a perspective view of another embodiment of the foot receptacle.

The second portion 122 may be rectilinear or curved. In an embodiment, the second portion comprises a curved portion 124 as shown in FIG. 4. The second portion may further comprise a drain hole 125 and a belt 126, if desired.

The foot rest 110 may further comprise a cross-member 130 disposed on a first (e.g., under) side of the first portion 121 of the foot receptacle 120 as shown in FIG. 1. The cross-member 130 may be fastened to the first side of the first portion 121 with a fastener. Representative fasteners include a screw, rivet, nail, pin, weld, adhesive, or a combination thereof.

Figure 5:
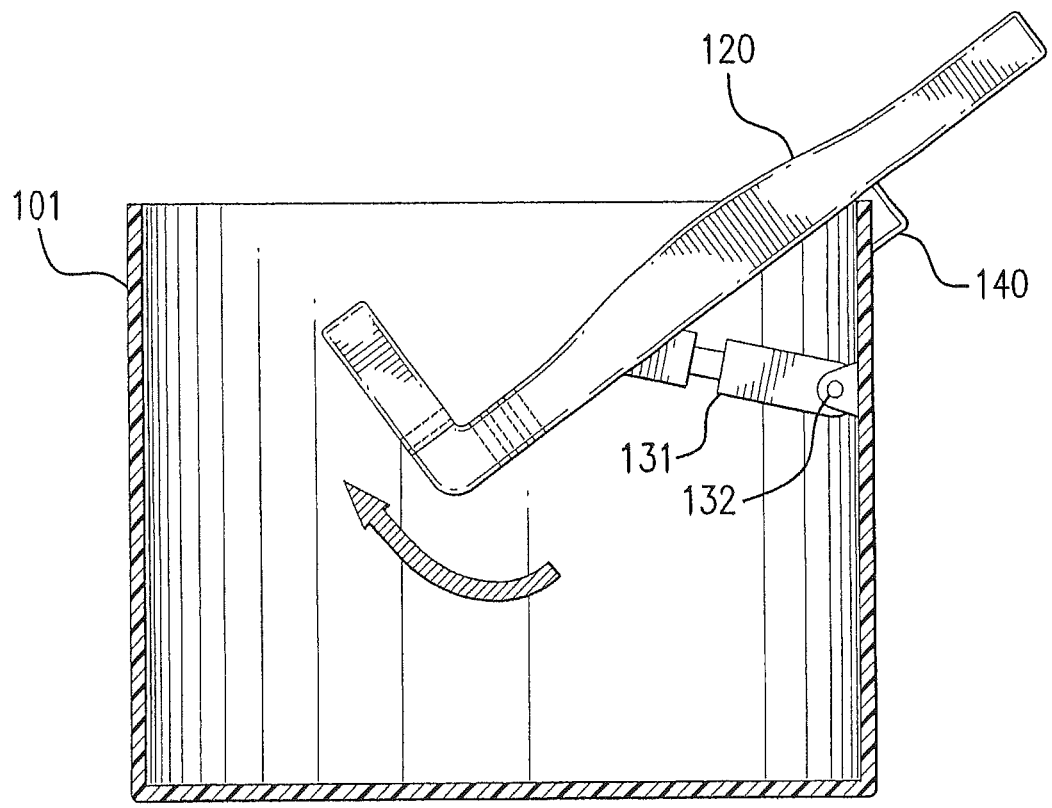
FIG. 5 is a schematic diagram showing inclination of a foot rest of the therapy device.

The cross-member may be telescopic or may be static (e.g., solid). A telescopic cross-member 131 is illustrated in FIG. 5. The telescopic cross-member may have a variable length, and may comprise a hinge 132 which allows the foot receptacle 120 to pivot with respect to a side of the bucket. The hinge 132 may be disposed distal to the foot receptacle, as is shown in FIG. 1, or may be disposed proximate to the foot receptacle. The telescopic cross-member 131 may have any suitable length, such as a length of about 5 cm to about 30 cm, specifically about 7 cm to about 20 cm. The telescopic cross-member may be ratcheted, and a length thereof may be selectable in about 3 cm increments.

Figure 6:
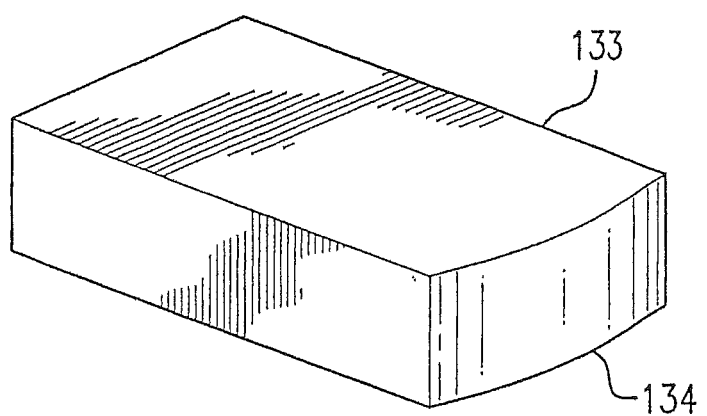
FIG. 6 is a perspective view of an embodiment of a cross-member.

A static cross-member 133 is further illustrated in FIG. 6. The static cross-member may be a single unitary indivisible part. The cross-member, e.g., the static cross-member 133, may have a curved-surface 134 which corresponds to an inner surface 103 of the bucket 101. The static cross-member may have a length of about 5 cm to about 30 cm, specifically about 7 cm to about 20 cm.

Figure 7:
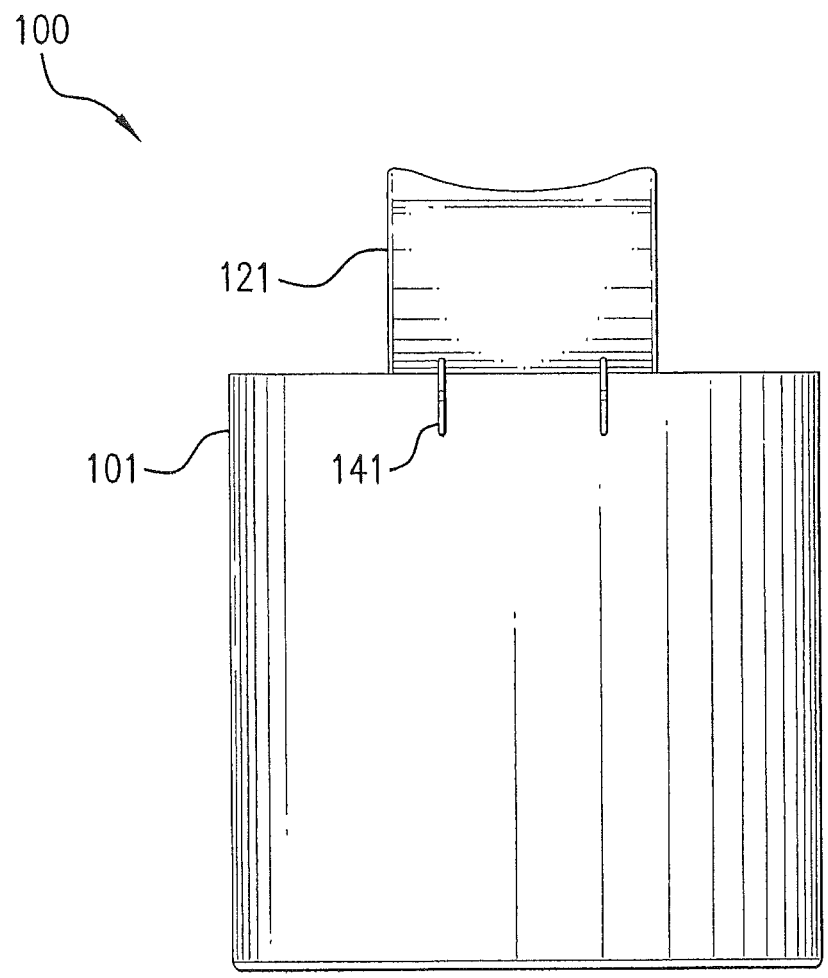
FIG. 7 is a rear view of an embodiment of the therapy device.
Figure 8:
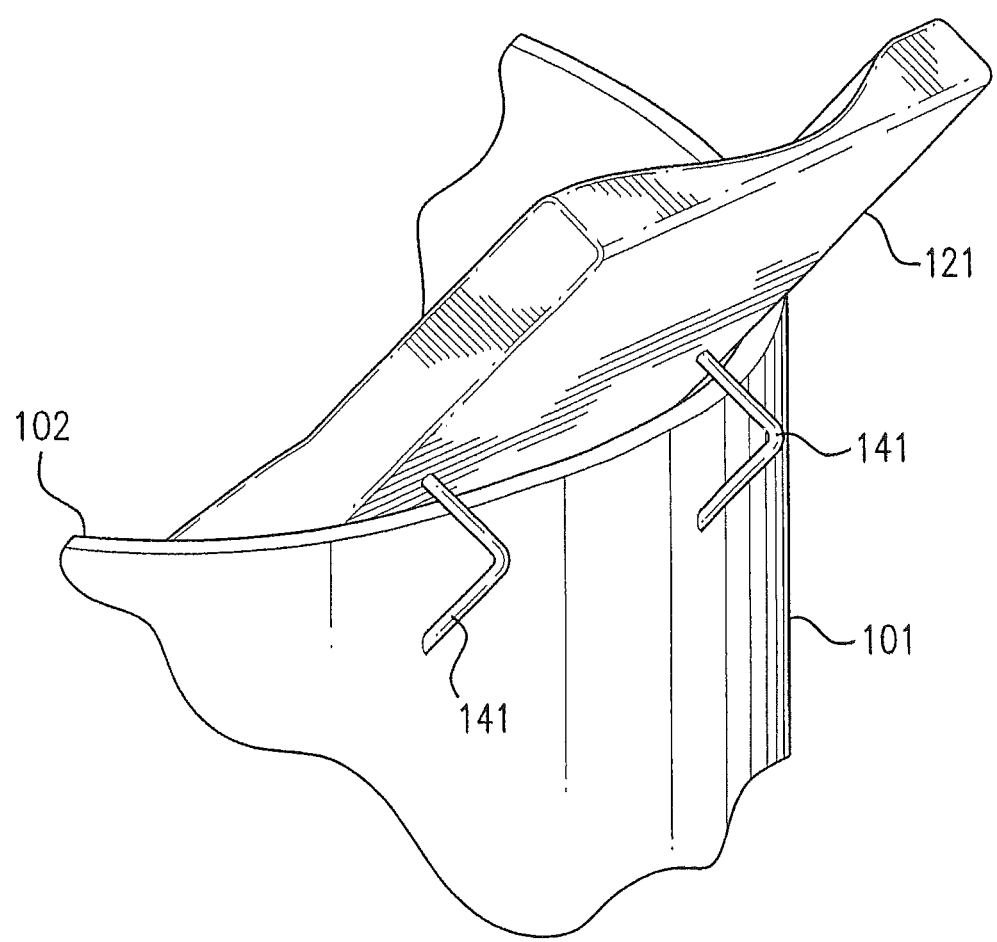
FIG. 8 is a rear perspective view of an embodiment of the therapy device.
Figure 9:
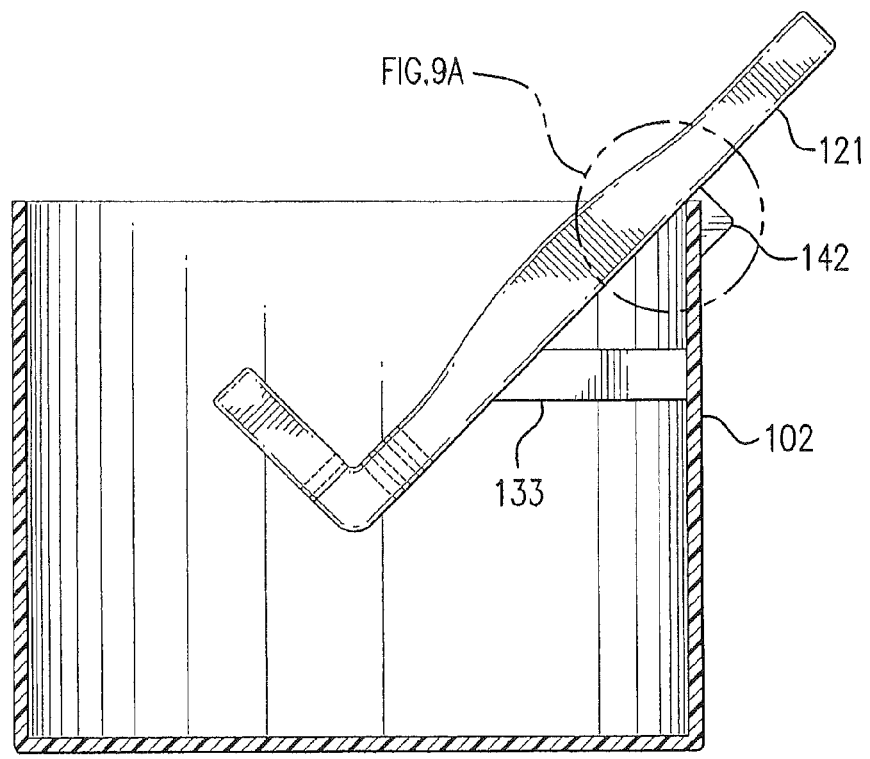
FIG. 9 is a schematic diagram of an embodiment of the therapy device.
Figure 9A:
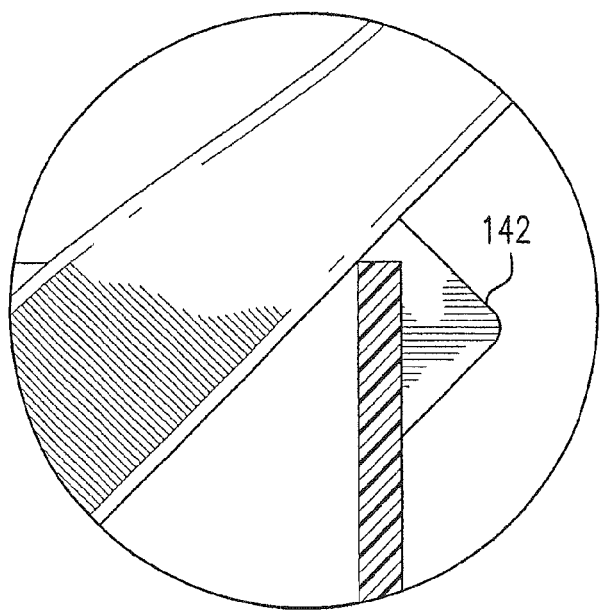
FIG. 9A is an enlarged view of a portion of FIG. 9.
Figure 9B:
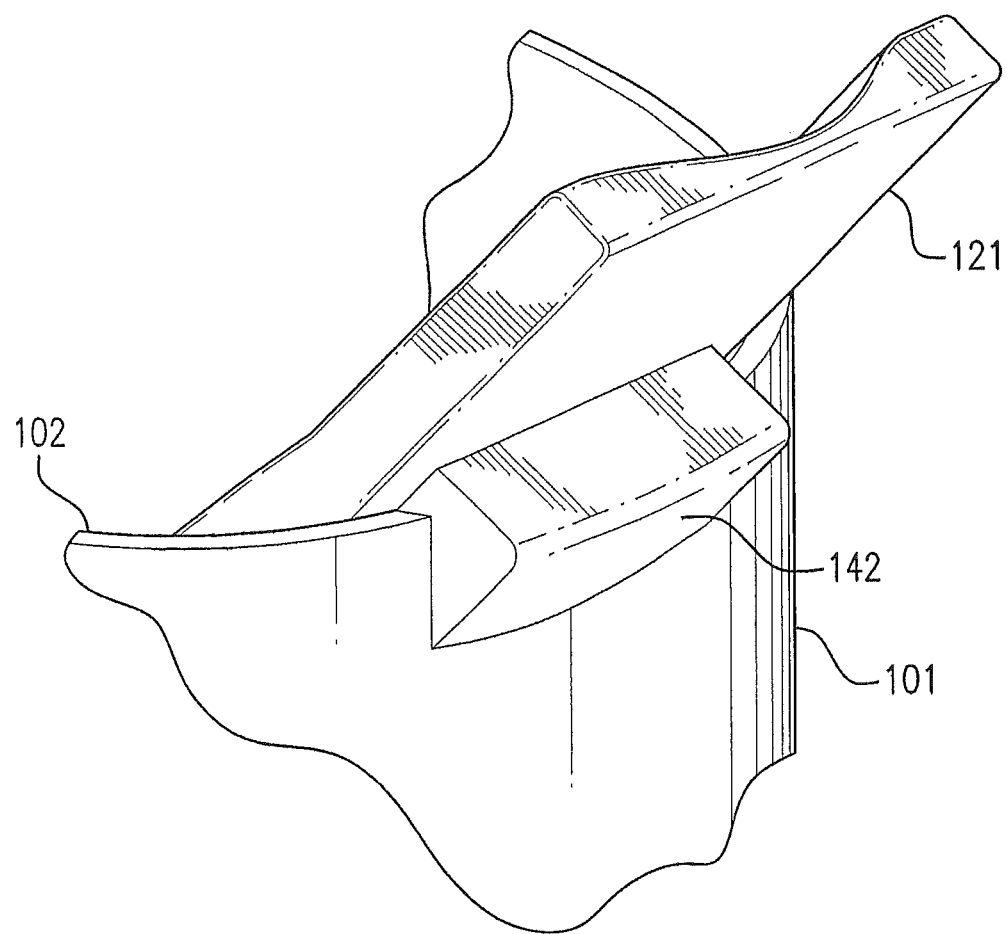
FIG. 9B is a rear perspective view of an embodiment of the therapy device.
Figure 10:
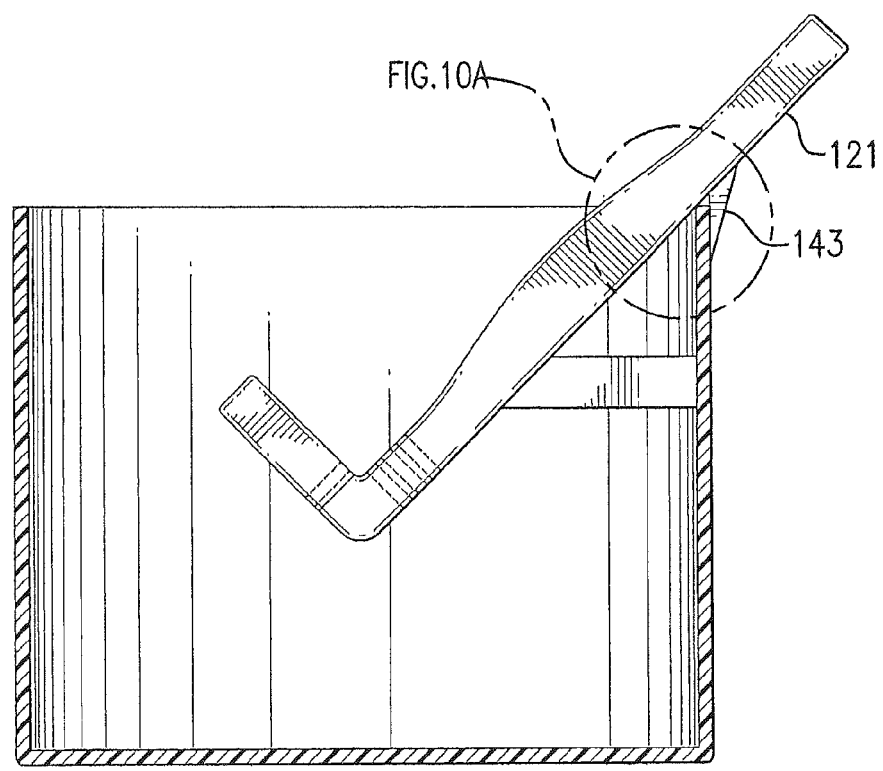
FIG. 10 is a schematic diagram of an embodiment of the therapy device.
Figure 10A:
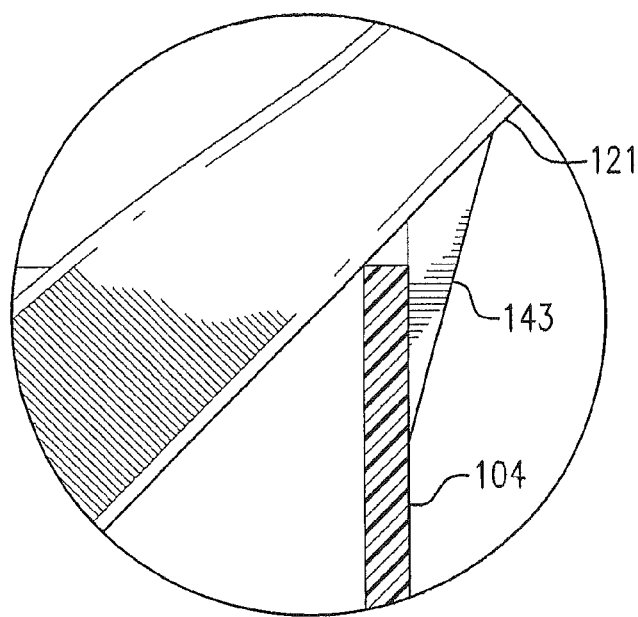
FIG. 10A is an enlarged view of a portion of FIG. 10.

The foot rest 110 further comprises a bucket connector 140 disposed on the first side of the first portion of the foot receptacle 120 and disposed distal to the end of the first portion. The bucket connector 140 may be configured to engage a rim 102 and an outer surface 104 of the bucket 101. The bucket connector may comprise a plurality of hooks 141 as shown in FIG. 7 for example, which is a rear view, and FIG. 8, which is a rear perspective view. The hooks 141 may be fastened to the first side of the first portion 121 of the foot receptacle 120. In another embodiment, the bucket connector is a shaped bucket connector 142 and is configured to engage the rim 102 and the outer surface 104 of the bucket as illustrated in FIGS. 9, 9A, and 9B. In yet another embodiment, the bucket connector is a scalene bucket connector 143 and is configured to engage the outer surface 104 of the bucket as illustrated in FIGS. 10, and 10A.

Figure 11:
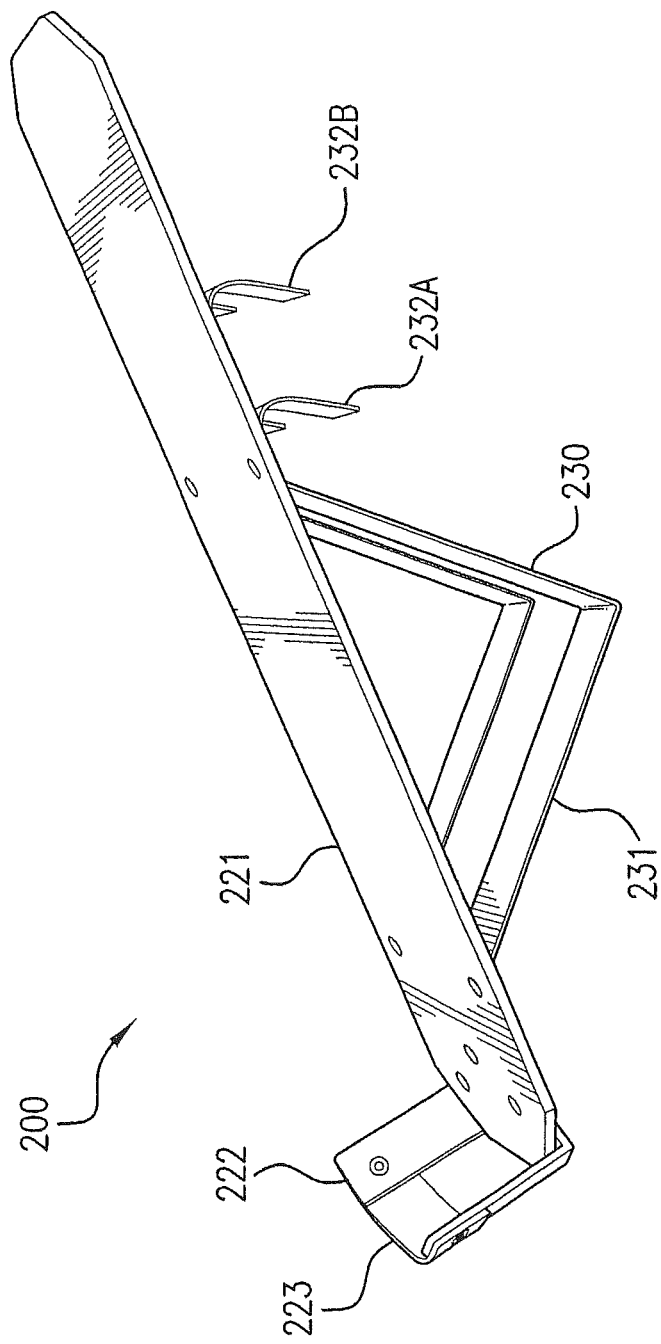
FIG. 11 is a schematic diagram of another embodiment of the foot rest.

In another embodiment, the foot rest may have the configuration shown in FIG. 11. In an embodiment, the foot rest 200 comprises a foot receptacle which comprises a first portion 221, a second portion 222, and a strap 223. In an embodiment, the foot receptacle comprises a plurality of second portions 222. The second portions 222 may be connected to an end of the first portion 221, and the strap 223 may connect the plurality of second portions 222. An embodiment comprising two second portions 222 is specifically mentioned. The first portion 221, the second portion 222, and the strap 223 may be connected using a fastener. Representative fasteners include a screw, rivet, nail, pin, weld, adhesive, or a combination thereof. An embodiment in which the first portion 221, the second portion 222, and the strap 223 are connected with rivets is specifically mentioned. As shown in FIG. 11, strap 223 may have a curved shape. In an embodiment, a plurality of second portions 222, the strap 223, and the first portion 221 form a cradle-shape.

In an embodiment, the cross-member and the bucket connector may be integrated to provide an integrated connector 230 as shown in FIG. 11. The integrated connector 230 may comprise a cross-member portion 231 and a bucket connector portion 232A and may be a single component. The integrated connector may be connected to the first portion 221 of the foot receptacle with a fastener. Representative fasteners include a screw, rivet, nail, pin, weld, adhesive, or a combination thereof. An embodiment in which the integrated connector 230 is fastened to the first portion 221 of the foot receptacle with a rivet is specifically mentioned. The cross-member portion 231 may be configured so that an end of the cross-member portion engages an inner surface 103 of the bucket, and the bucket connector portion 232A may be configured to engage the rim 102 of the bucket. The bucket connector may optionally also engage an outer surface 104 of the bucket. In an embodiment, a plurality of bucket connectors is provided. For example, in an embodiment an additional bucket connector 232B may be disposed on the first portion 221. The bucket connector portion 232A may be disposed a first distance from an end of the first portion 221, and the additional bucket connector portion 232B may be disposed a second distance from the end of the first portion 221, wherein the first distance and the second distance are different. Thus a series of bucket connectors may be disposed on the first portion 221 at different distances from the end of the first portion 221 so that the foot rest 200 may be suitably used with buckets having different depths and/or sides having different slopes.

The foot receptacle, the cross-member, the bucket connector, and the integrated connector may each independently comprise any suitable material, including and without limitation a plastic, rubber, metal, wood, ceramic, composite, or a combination thereof. Suitable plastics and metals are further disclosed above. An embodiment in which the foot rest comprises an aluminum alloy is specifically mentioned. In an embodiment, the metal, e.g., aluminum is coated with a plastic, e.g., a vinyl coating. In another embodiment, the foot rest comprises a glass filled polypropylene.

The foot rest may comprise any suitable material, including and without limitation a plastic, rubber, metal, wood, ceramic, composite, or a combination thereof. In an embodiment, the foot rest is a single unitary indivisible part. An embodiment wherein the foot rest consists of a single material, e.g., a glass filled polyolefin such as a glass filled polypropylene, is specifically mentioned. In an embodiment, the foot rest may be molded. An embodiment in which the foot rest comprises a polycarbonate and is a product of molding is specifically mentioned.

Figure 12:
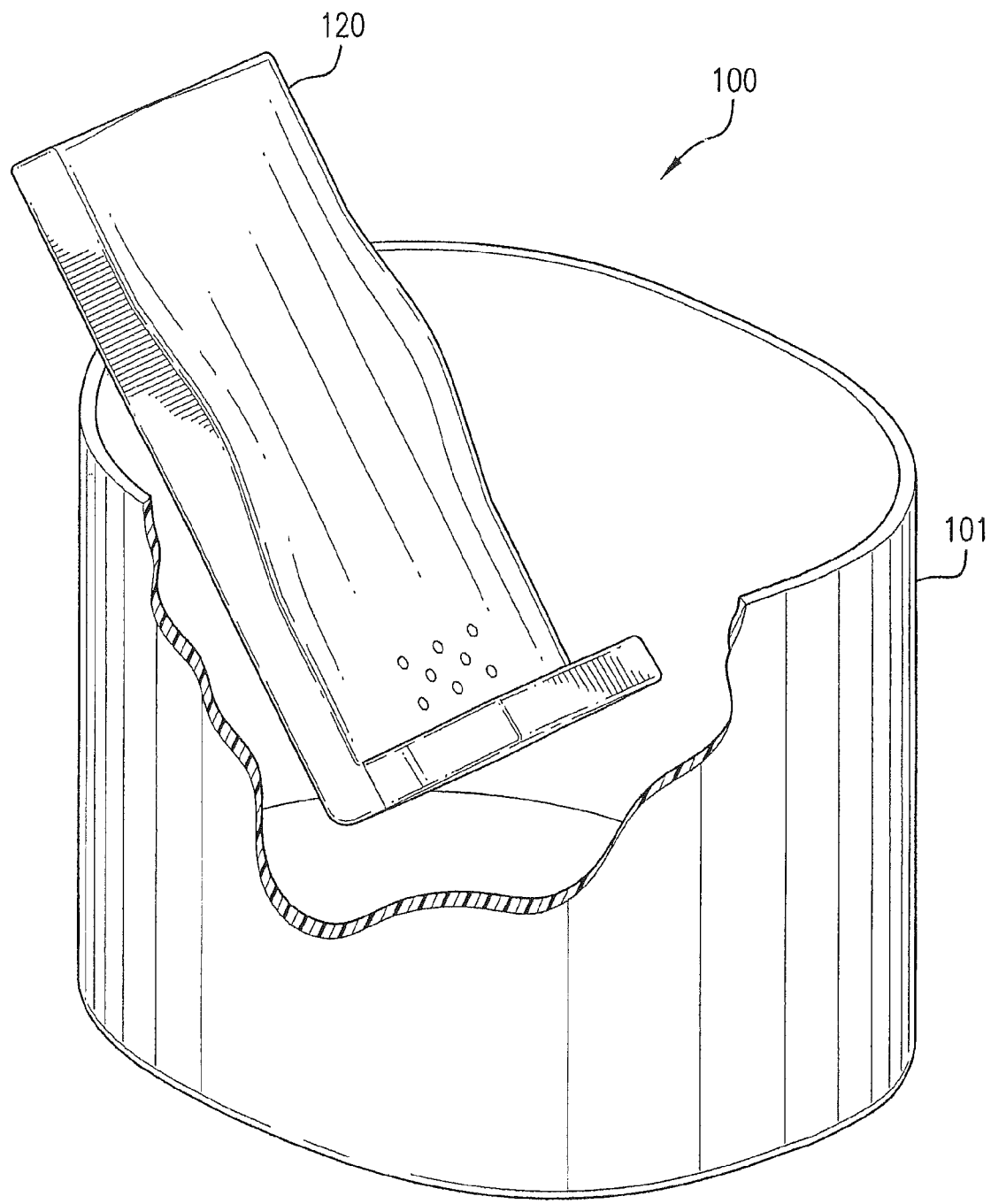
FIG. 12 is a schematic diagram of the foot rest on the bucket.

To assemble a therapy device, the foot rest may be disposed on a bucket, as shown in FIG. 12. When disposed on the bucket, the cross-member and bucket connector engage the inner surface and rim of the bucket, respectively, to provide the first portion of the foot receptacle at an angle of about 20° to about 80°, specifically about 30° to about 60°, more specifically about 35° to about 50° with respect to the inner surface of the bucket. The foot rest may simply rest on the bucket, or may be fastened to the bucket with a fastener. Representative fasteners include a screw, rivet, nail, pin, weld, adhesive, or a combination thereof.

Alternatively, the bucket and the foot rest may be a single unitary indivisible part, as may be provided by molding, for example. In an embodiment, the therapy device comprises of a plastic, a rubber, a metal, or a combination thereof. An embodiment wherein the therapy device consists of polycarbonate or polyethylene is specifically mentioned.

Also disclosed is a method of manufacturing the foot rest. The method comprises providing a foot receptacle, the foot receptacle comprising a first portion and a second portion, wherein the first portion intersects the second portion; disposing a cross-member on a first side of the first portion, wherein the cross-member is proximate an end of the first portion; and disposing a bucket connector on the first side of the first portion of the foot support, wherein the bucket connector is distal to the end of the first portion to manufacture the foot rest for therapy.

To assemble a therapy device, the foot rest may be disposed on a bucket.

Alternatively, at least one of the bucket and the foot rest may be produced by molding or stamping. Methods of molding include injection molding, extrusion molding, and blow molding. Stamping can include stamping a metal or a plastic. An embodiment in which the therapy device consists of polycarbonate or polyethylene and is a molded product is specifically mentioned.

Also disclosed is a method of therapy, the method comprising: providing the therapy device comprising the foot rest and the bucket; disposing a composition having a temperature of −20° C. to 50° C. in the bucket; and immersing an ankle in the composition to administer therapy to the ankle.

The composition may consist of a liquid, or may comprise a combination of a liquid and a solid. The liquids may comprise water, oil, glycerin, ethylene glycol, propylene glycol, salt water, or a combination thereof. An embodiment in which the liquid is water is specifically mentioned. Representative solids include the solid forms of water, oil, glycerin, ethylene glycol, propylene glycol, salt water, or a combination thereof. An embodiment in which the composition is a combination of liquid water and ice, i.e., ice water, is specifically mentioned.

The bucket may be filled with an amount of the composition sufficient to immerse the heel, the ankle, or the entire foot, as desired. In an embodiment, the bucket is filled with an amount of the composition sufficient to immerse the ankle and not immerse the toes. An embodiment where the bucket is filled with an amount of the composition sufficient to immerse the foot to the top of the arch is specifically mentioned. This permits treatment of the ankle while avoiding undesirable treatment of the toes. Thus, in an embodiment where cryotherapy with ice water is used, for example, the toes may remain above the level of the ice water while the ankle is immersed and treated. Avoiding treatment of the toes can result in improved comfort.

The method of therapy may include cryotherapy, in which case a composition having a temperature less than 20° C. may be used, or thermotherapy, in which case a composition having a temperature greater than 20° C. may be used. The composition may have a temperature of about −20° C. to about 50° C., specifically about −10° C. to about 5° C., more specifically about −5° C. to about 3° C., or about 30° C. to about 45° C., more specifically about 35° C. to about 40° C. Also, the temperature of the composition may be selected during treatment by addition of a fluid having a different temperature, by immersion of a heater, or immersion of a cooler, for example. In an embodiment the temperature of the composition is controlled by an immersion circulator or a recirculating circulator.

Figure 13:
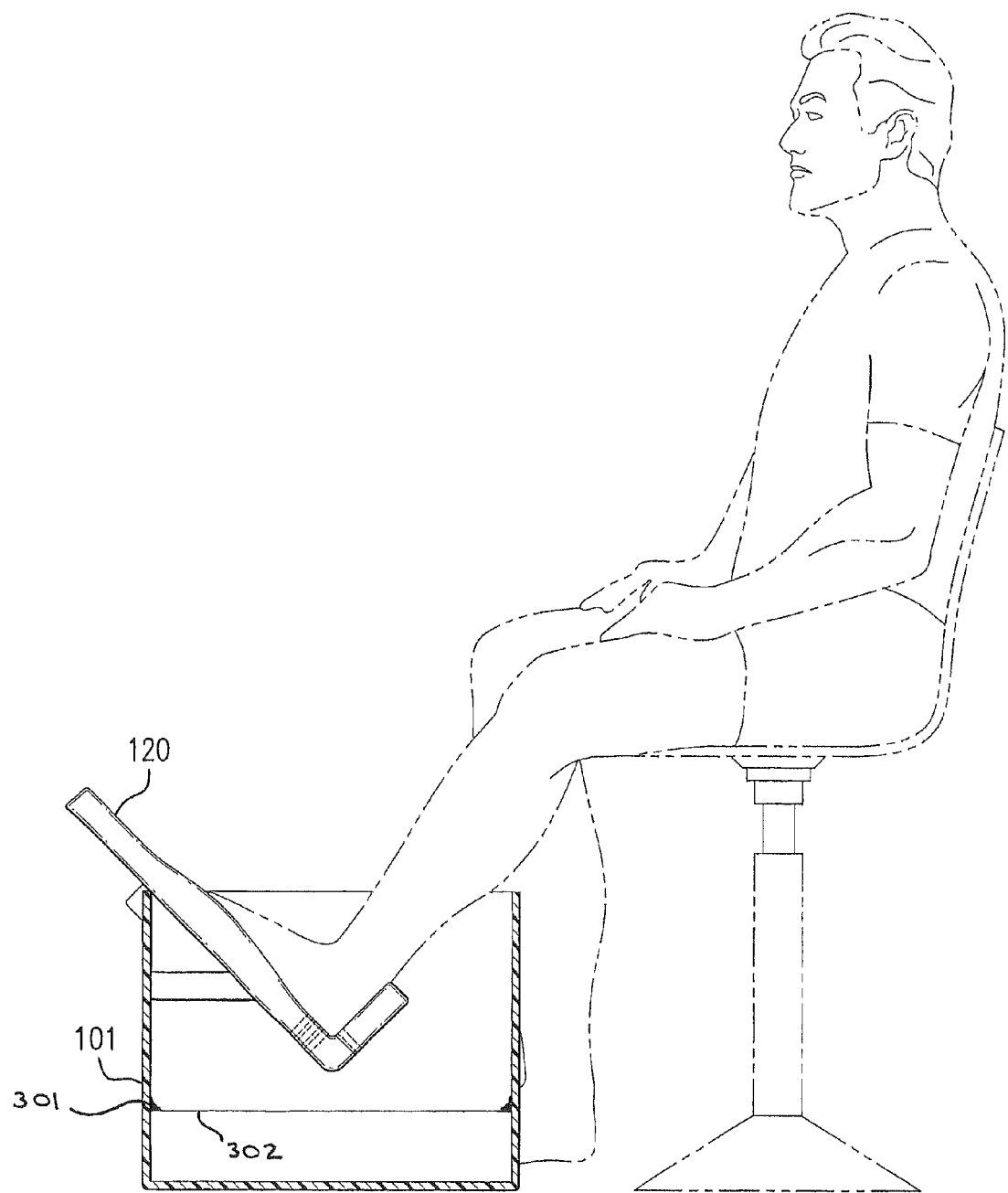
FIG. 13 is a schematic diagram of an embodiment of a method of therapy.
Figure 14:
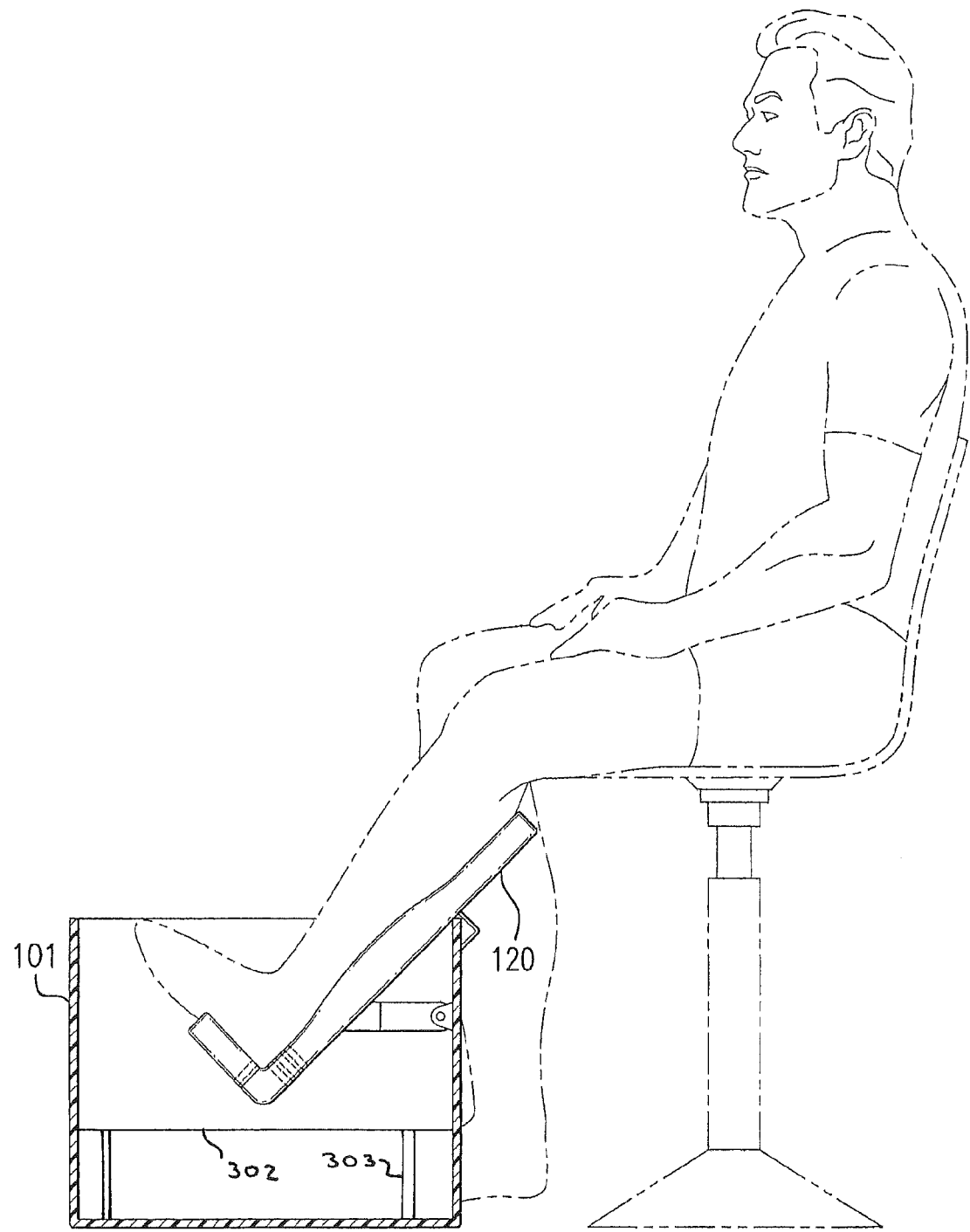
FIG. 14 is a schematic diagram of another embodiment of a method of therapy.

The foot rest may be used in at least two configurations as illustrated in FIGS. 13 and 14. In a first configuration, the user may place the sole of the foot on the first portion of the foot receptacle. In a second configuration, the user may place the sole of the foot on the second portion of the foot receptacle. In either configuration, the foot rest comfortably supports the foot and lower leg, providing improved comfort and convenience. Furthermore, the therapy device avoids contact of the foot or lower leg with the bucket, thereby avoiding discomfort which could occur if the leg were to contact the rim of the bucket, for example. Further still, the therapy device allows administration of cryotherapy or thermotherapy while the user is comfortable and safely seated.

The therapy device may further comprise a screen 302. The screen 302 may be disposed underneath the foot rest to prevent ice from contacting the skin of the user, thereby further improving comfort. A mesh size of the screen is not specifically limited, and may be selected depending on a size of ice selected. A screen having an average opening dimension of 1 to 100 millimeters (mm), specifically 5 to 50 mm may be used. The screen may span the width of the bucket and may be disposed to provide a top portion and a bottom portion. In an embodiment, ice is disposed in the bottom portion. The screen may be retained with a lip 301 which is disposed on an inner surface of the bucket.

In another embodiment, the screen may be supported with legs 303 that rest on the bottom of the bucket. In yet another embodiment, the screen may be wrapped around the foot rest and the user's foot to prevent ice from contacting the foot or leg.

The screen may comprise any suitable material, such as a metal or a plastic. An aluminum screen and a fiberglass screen are specifically mentioned.

In an embodiment disclosed is a foot rest comprising: a foot receptacle, the foot receptacle comprising a first portion and a second portion, wherein the first portion intersects the second portion; a cross-member disposed on a first side of the first portion; and a bucket connector disposed on the first side of the first portion of the foot receptacle, wherein the cross-member is proximate an end of the first portion and the bucket connector is distal to the end of the first portion.

In various embodiments, (1) the first portion and the second portion of the foot support are perpendicular; and/or (2) the first portion is contoured such that a middle portion of an edge of the first portion is thicker than an end portion of the first portion and thicker than a middle portion of the first portion; and/or (3) the foot rest is a single unitary indivisible part; and/or (4) the cross-member is connected to the first side of the first portion with a fastener; and/or (5) the cross-member is extendable and further comprises a hinge; and/or (6) the bucket connector comprises a hook disposed on the first side of the first portion of the foot support; and/or (7) the cross-member and the bucket connector are a single unitary indivisible part.

Also, a therapy device comprises a bucket; and the foot rest disposed on the bucket, wherein the bucket connector engages a rim of the bucket and the cross-member engages an inner surface of the bucket.

In various embodiments, (1) the therapy device is a single unitary indivisible part; and/or (2) the cross-member is fastened to the inner surface of the bucket with a fastener; and/or (3) the fastener is a screw, a rivet, a nail, a hook-and-loop fastener, or an adhesive.

While embodiments have been set forth for the purpose of illustration, the foregoing descriptions should not be deemed to be a limitation on the scope herein. Accordingly, various modifications, adaptations, and alternatives can occur to one skilled in the art without departing from the spirit and scope herein. In addition, modifications can be made to adapt a particular situation or material to the teachings of this disclosure without departing from the essential scope thereof. Therefore, it is intended that the invention not be limited to the particular embodiment disclosed as the best mode contemplated for carrying out the disclosed method. Descriptions of features, aspects, or advantages of each embodiment should be considered as available for other similar features, aspects, or advantages of other embodiments.

What is claimed is:

1. A therapy device comprising,
   a bucket; and
   a foot rest disposed on the bucket, the foot rest comprising
      a foot receptacle, the foot receptacle comprising a first portion and a second portion, wherein the first portion intersects the second portion;
      a cross-member disposed on a first side of the first portion; and
      a bucket connector disposed on the first side of the first portion of the foot receptacle,
   wherein the cross-member is proximate an end of the first portion and the bucket connector is distal to the end of the first portion, and
   wherein the bucket connector engages a rim of the bucket and the cross-member engages an inner surface of the bucket.

2. The therapy device of claim 1, wherein the first portion and the second portion of the foot receptacle are perpendicular.

3. The therapy device of claim 1, wherein the first portion is contoured such that a middle portion of an edge of the first portion is thicker than an end portion of the first portion and thicker than a middle portion of the first portion.

4. The therapy device of claim 1, wherein the foot rest is a single unitary indivisible part.

5. The therapy device of claim 1, wherein the cross-member is connected to the first side of the first portion with a fastener.

6. The therapy device of claim 1, wherein the cross-member is extendable and further comprises a hinge.

7. The therapy device of claim 1, wherein the bucket connector comprises a hook disposed on the first side of the first portion of the foot receptacle.

8. The therapy device of claim 7, wherein the cross-member and the bucket connector are a single unitary indivisible part.

9. The therapy device of claim 1, wherein the therapy device is a single unitary indivisible part.

10. The therapy device of claim 1, wherein the cross-member is fastened to the inner surface of the bucket with a fastener.

11. The therapy device of claim 10, wherein the fastener is a screw, a rivet, a nail, a hook-and-loop fastener, or an adhesive.

12. A method of therapy, the method comprising:
    providing the therapy device of claim 1;
    disposing a composition having a temperature of about −20° C. to about 50° C. in the bucket; and
    immersing an ankle in the composition to administer therapy to the ankle.

13. The method of therapy of claim 12, wherein the composition is ice water.

14. A method of manufacturing a foot rest for therapy, the method comprising molding the therapy device of claim 1.

15. A therapy device comprising:
a bucket;
a foot rest on the bucket, the foot rest comprising
- a foot receptacle having a first portion and a second portion, wherein the first portion intersects the second portion to form a cradle; and
- a cross-member connecting the foot receptacle and the bucket, wherein the bucket, the foot rest, and the cross-member are a single unitary indivisible part.

16. The therapy device of claim 15, wherein the first portion and the second portion form an angle of about 120° to about 80°.

17. The therapy device of claim 16, wherein an angle between the first portion and an inner surface of the bucket is about 35° to about 50°.

18. A method of assembling a therapy device, the method comprising:
- providing a foot receptacle, the foot receptacle comprising a first portion and a second portion, wherein the first portion intersects the second portion;
- disposing a cross-member on a first side of the first portion, wherein the cross-member is proximate an end of the first portion; and
- disposing a bucket connector on the first side of the first portion of the foot receptacle, wherein the bucket connector is distal to the end of the first portion to manufacture a foot rest for therapy, and then
- disposing the foot rest on a bucket to assemble the therapy device.

* * * * *